United States Patent
Kouou (10) Patent No.: US 6,752,760 B2
(45) Date of Patent: Jun. 22, 2004

(54) APPARATUS FOR MEASURING VISCERAL FAT

(75) Inventor: Takahito Kouou, Tokyo (JP)

(73) Assignee: Tanita Corporation, Tokyo (JP)

( * ) Notice: Subject to any disclaimer, the term of this patent is extended or adjusted under 35 U.S.C. 154(b) by 200 days.

(21) Appl. No.: 10/113,295

(22) Filed: Apr. 2, 2002

(65) Prior Publication Data

US 2002/0151803 A1 Oct. 17, 2002

(30) Foreign Application Priority Data

Apr. 11, 2001 (JP) .......................... 2001-112917

(51) Int. Cl.$^7$ .............................................. A61B 5/00
(52) U.S. Cl. ...................... 600/301; 600/485; 600/500; 600/547
(58) Field of Search ............... 600/300–301, 600/485–507, 547

(56) References Cited

U.S. PATENT DOCUMENTS

| | | | |
|---|---|---|---|
| 5,579,782 A | * 12/1996 | Masuo | 600/547 |
| 6,321,112 B1 | * 11/2001 | Masuo | 600/547 |
| 6,327,495 B1 | * 12/2001 | Iwabuchi et al. | 600/547 |
| 6,487,445 B1 | * 11/2002 | Serita et al. | 600/547 |
| 6,516,221 B1 | * 2/2003 | Hirouchi et al. | 600/547 |
| 6,526,315 B1 | * 2/2003 | Inagawa et al. | 600/547 |

FOREIGN PATENT DOCUMENTS

| | | |
|---|---|---|
| DE | 19639095 A1 | 3/1998 |
| EP | 1 063 500 A2 | 12/2000 |
| WO | WO 01/91638 A1 | 12/2001 |

OTHER PUBLICATIONS

U.S. patent application Ser. No. 09/590,675, Serita et al., filed Jun. 9, 2000.

* cited by examiner

Primary Examiner—Robert L. Nasser
Assistant Examiner—Patricia Mallari
(74) Attorney, Agent, or Firm—McDermott, Will & Emery (57) ABSTRACT

Disclosed is an apparatus for measuring visceral fat, comprising an input unit, a bioelectrical impedance measuring unit, a blood pressure measuring unit, and an arithmetic unit. The input unit enters body information regarding a body of a person to be measured. The bioelectrical impedance measuring unit measures the bioelectrical impedance of the person. The blood pressure measuring unit measures the blood pressure of the person. The arithmetic unit calculates the visceral fat value of the person, based on the entered body information, the measured bioelectrical impedance and the measured blood pressure.

9 Claims, 10 Drawing Sheets

Height: 170cm
Body Weight : 75kg
Body Fat Ratio: 25%

Visceral Fat Area: 65cm$^2$
Systolic Blood Pressure: 60mmHg
Diastolic Blood Pressure:120mmHg
Pulse Rate: 70/min
Morbidity Index 2.0 point/person

| | Without Exercise | With Exercise |
|---|---|---|
| No Weight Reduction | Corpulent Person:<br>Reduce weight by a diet with an exercise.<br>Normal Person:<br>Do light exercise. | Corpulent Person:<br>To make a diet is more effective.<br>Normal Person:<br>Keep this condition. |
| Weight Reduced | Corpulent Person:<br>Do exercise.<br>Reducing the weight only by a diet adversely affects your health. | Corpulent Person:<br>Good weight reduction.<br>Keep this condition. |

FIG. 9

Height: 170cm
Body Weight : 75kg
Body Fat Ratio: 25%

Visceral Fat Area: 65cm$^2$
Systolic Blood Pressure: 60mmHg
Diastolic Blood Pressure:120mmHg
Pulse Rate: 70/min
Morbidity Index 2.0 point/person "Do some exercises. Reducing the weight only by a diet adversely affects your health."

FIG. 10

APPARATUS FOR MEASURING VISCERAL FAT

BACKGROUND OF THE INVENTION

1. Field of the Invention

The present invention relates to measurement of visceral fat of a person to be measured, and more particularly, to a technique for measuring the visceral fat of the person with higher precision.

2. Prior Art

A body fat meter for estimating body fat ratio representing the rate of body fat occupying the body of a person using a bioelectrical impedance method has been known as the apparatus that allows facilitated measurement of the health condition at home. Another measurement apparatus such as a blood pressure meter, a pulse meter, etc., have also been put into the market and utilized by those people who take care of the health condition.

An additional apparatus that is capable of measuring a plurality of measurable parameters of the person has also been proposed.

In this connection it is noted that the body fat is classified into two types: subcutaneous fat that is present under the skin mainly in the parts such as an abdomen or legs; and visceral fat that is present around intraperitoneal organs (in portal system such as mesentery and omentum majus). Recently it becomes considered as an essential matter that the amount of visceral fat is greater relative to the total body fat because it leads to occurrence of a complication such as diabetes, myocardial infarction, etc. A method that has been conducted in the special hospitals for knowing the amount of visceral fat is to take a picture of an abdomen using X-ray CT scanner and to calculate the visceral fat area based on the tomographic image of the navel region.

In general, a clinical experiment such as a blood test or a urine analysis is conducted in the hospital and a plurality of resultant data is used to calculate the prevalence rate for determining any possibility of occurrence of the complication.

However, the method of calculating the visceral fat area using the X-ray CT, as described above, is defective in that it makes a person to be measured felt uneasy because he is exposed to a radiation, but in small amount. In addition, the apparatus for embodying the method is rather bulky so that it is not easy to perform the measurement.

The body fat meter generally known in the art for estimating the body fat of a person to be measured using bioelectrical impedance produces a total body fat across the part to be measured without distinguishing between subcutaneous fat and visceral fat. Therefore, a method of estimating the visceral fat area based on bioelectrical impedance has been proposed in which the height, body weight, age, sex and girth of the waist of a person to be measured can be used as the parameters to produce a visceral fat value. However, it has been still desired to more precisely calculate the visceral fat value.

The prevalence rate has been produced by analysis of the data generally obtained by the clinical experiment conducted in the hospital, as described above. It involves some skilled persons and takes longer period of time for calculation.

It has been said that the visceral fat is more likely to be reduced, as compared to the subcutaneous fat, if the weight reduction with proper exercise is conducted, in addition to the weight reduction with proper diet. However, any excessive weight reduction by only the diet without any exercise causes significant reduction of fat free mass so that an improvement in blood pressure and pulse rate due to the reduction of body fat is lower than the case where the weight reduction is conducted by the diet with the exercise.

Furthermore, such weight reduction entails the rebound of body weight, and consequently, it may cause and sustain higher blood pressure condition for longer period of time. This becomes a problem, even if the body weight is temporally reduced.

In view of the above the present invention is directed to simple, but highly precise estimation of value of visceral fat by measuring parameters relating to change in visceral fat and using the measured parameters for estimation of the visceral fat.

In addition, the prevalence rate or morbidity index of a person to be measured is calculated, based on the estimated visceral fat area, etc.

Furthermore, it is determined whether the proper weight reduction has been conducted or not, based on the change in visceral fat. A check is also performed in order not to conduct any improper weight reduction.

SUMMARY OF THE INVENTION

According to one aspect of the present invention there is provided an apparatus for measuring visceral fat, comprising: an input unit; a bioelectrical impedance measuring unit; a blood pressure measuring unit; and an arithmetic unit, whereby said input unit enters personal data regarding a body of a person to be measured, said bioelectrical impedance measuring unit measures the bioelectrical impedance of the person, said blood pressure measuring unit measures the blood pressure of the person, and said arithmetic unit calculates the value of visceral fat of the person, based on the entered personal data, the measured bioelectrical impedance and the measured blood pressure.

According to another aspect of the present invention there is provided an apparatus for measuring visceral fat, comprising: an input unit; a bioelectrical impedance measuring unit; a pulse rate measuring unit; and an arithmetic unit, whereby said input unit enters personal data regarding a body of a person to be measured, said bioelectrical impedance measuring unit measures the bioelectrical impedance of the person, said pulse rate measuring unit measures the pulse rate of the person, and said arithmetic unit calculates the value of visceral fat of the person, based on the entered personal data, the measured bioelectrical impedance and the measured pulse rate.

According to further aspect of the present invention there is provided an apparatus for measuring visceral fat, comprising: an input unit; a bioelectrical impedance measuring unit; a blood pressure measuring unit; a pulse rate measuring unit; and an arithmetic unit, whereby said input unit enters personal data regarding a body of a person to be measured, said bioelectrical impedance measuring unit measures the bioelectrical impedance of the person, said blood pressure measuring unit measures the blood pressure of the person, said pulse rate measuring unit measures the pulse rate of the person, and said arithmetic unit calculates the value of visceral fat of the person, based on the entered personal data, the measured bioelectrical impedance, the measured blood pressure and the measured pulse rate.

The apparatus for measuring visceral fat according to the present invention calculates prevalence rate of the person to be measured, based on at least one of the measured blood pressure and pulse rate, and the calculated value of visceral fat.

The apparatus for measuring visceral fat according to the present invention further comprises a memory unit and an evaluation unit, whereby said memory unit stores at least one of the measured blood pressure and pulse rate, and the calculated value of visceral fat, and said evaluation unit evaluates reduced weight condition, based on the previous value of visceral fat and at least one of the blood pressure and pulse rate stored in the memory unit, as well as the calculated current value of visceral fat and at least one of the blood pressure and pulse rate.

In the apparatus for measuring visceral fat according to the present invention said value of visceral fat is of visceral fat area.

The apparatus for measuring visceral fat according to the present invention further comprises a body weight meter that measures the body weight of the person, and the measured body weight is used for calculating the visceral body fat.

The apparatus for measuring visceral fat further comprises a display unit by which at least one of the measured blood pressure and pulse rate as well as the calculated value of visceral fat is displayed in the form of radar chart.

The apparatus for measuring visceral fat further comprises a display unit by which an advice message according to the evaluation result for reduced weight condition is displayed.

BRIEF DESCRIPTION OF THE DRAWINGS

Now, the present invention will be described in more detail with reference to the accompanying drawings, in which.

DESCRIPTION OF THE PREFERRED EMBODIMENT

It has been said that the visceral fat is deeply related to the blood pressure and the pulse rate. The mechanism is such that if the visceral fat increases a large amount of free fatty acid (FFA) flows through the portal system into the liver to increase a fat compounding and to cause an insulin resistance. As the body fat ratio increases the systolic blood pressure (lowest blood pressure) is increased along with the diastolic blood pressure (highest blood pressure), which may cause a hypertension.

It has also been said that the body fat ratio, BMI, visceral fat area, etc., are intimately related to various diseases. The diseases that a person could suffer from when he has higher value of the body fat ratio, BMI, visceral fat area, etc., are not only the hypertension, but also the hepatopathy, hyperlipidemia (hypercholesterolemia), hyperuricemia, cardiac disease, abnormal glucose metabolism, stomach and duodenum disease, etc.

Figure 1:
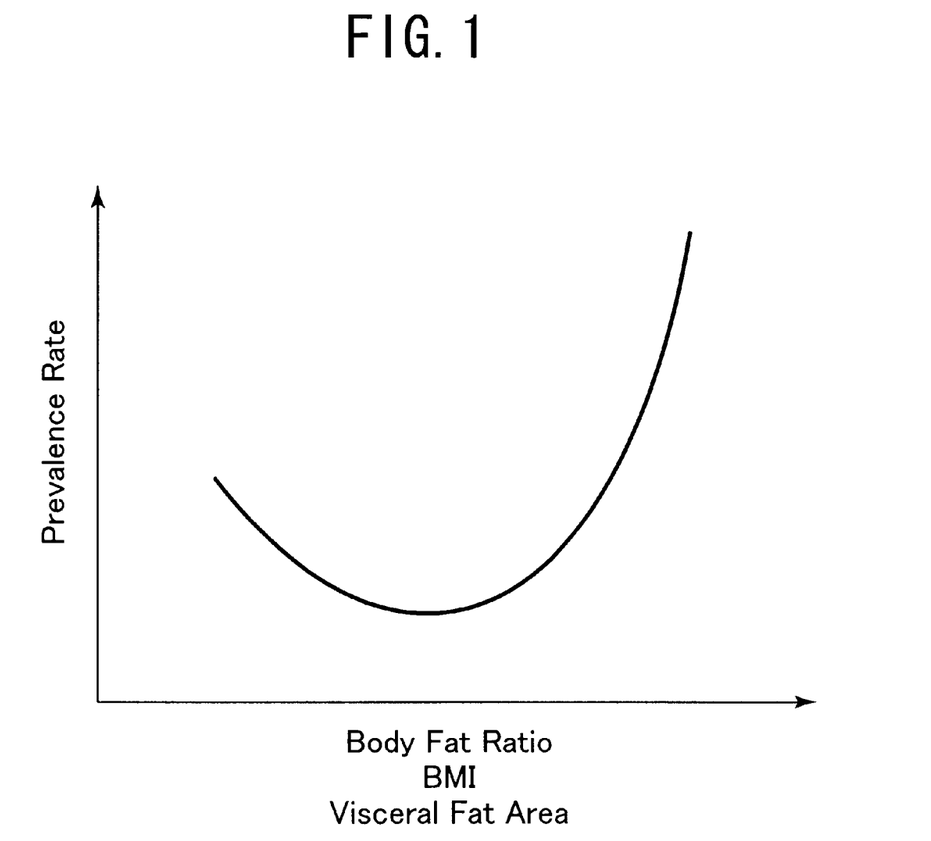
FIG. 1 is a graph showing a tendency of prevalence rate.

In particular, as the body fat ratio, visceral fat area, and BMI increases, there is such tendency that the prevalence ratio becomes higher. FIG. 1 shows the relationship between the prevalence rate and the body fat ratio, BMI and visceral fat ratio. The prevalence rate is represented in the form of quadratic "J" curve. Accordingly it is not preferable that the visceral fat area and BMI have too large values or too small values. Instead, they must have such values that are suitable for individual persons. The prevalence ratio should be paid great attention because increasing the prevalence ratio entails an increase in rate of complication.

Figure 2:
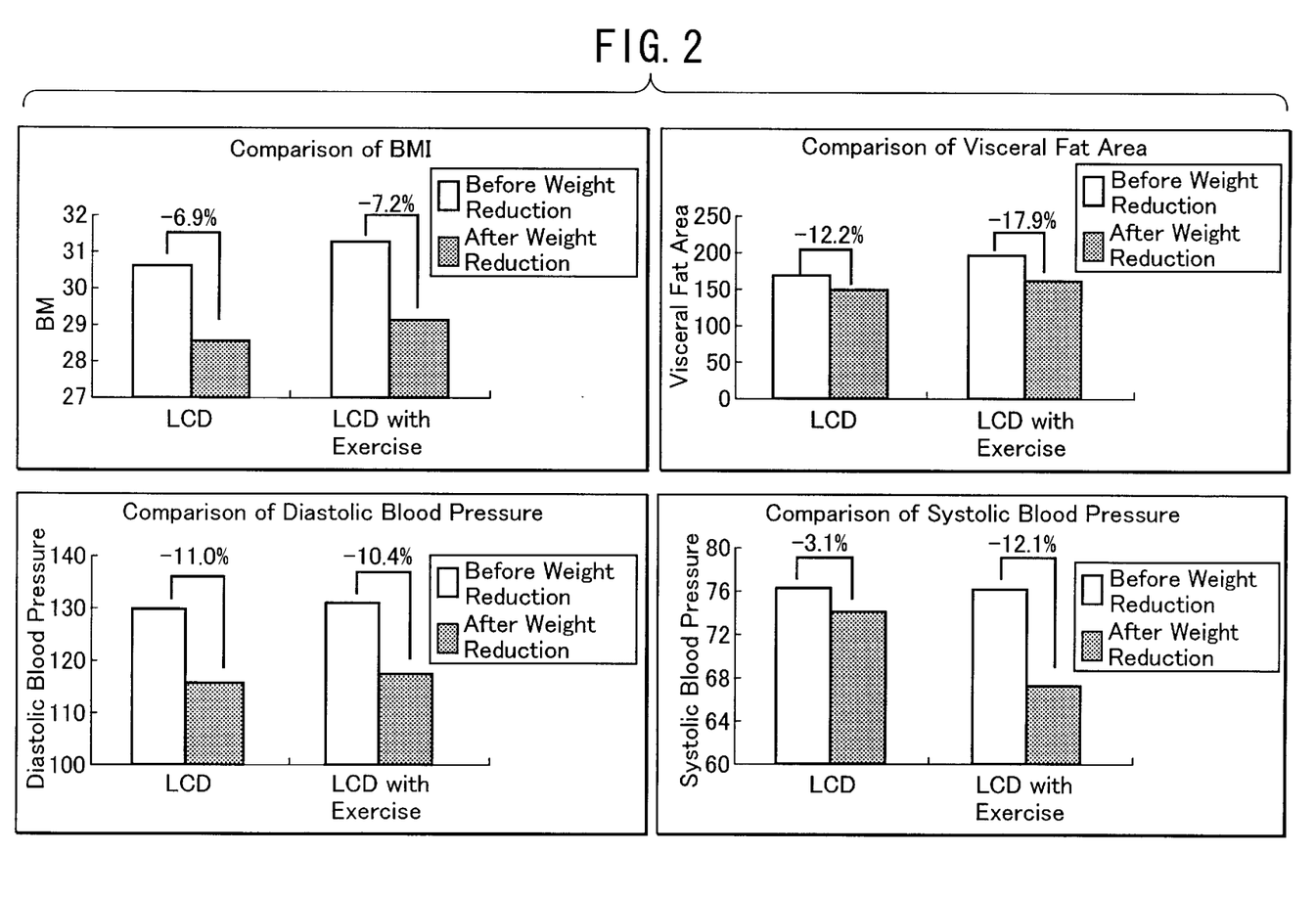
FIG. 2 is a graph showing the difference in reduction of body weight for two different cases: one is to make only a low-calorie diet (LCD) and the other is to make both LCD and a proper exercise.

It is important for body weight reduction that limitation of intake calories in a meal (or making a diet) is efficiently combined with making an exercise. FIG. 2 shows reduction in value of each of parameters resulted after one month has been passed for two different ways of body weight reduction: one is to make only a low-calorie diet (LCD) and the other is to make both LCD and a proper exercise. As can be seen in FIG. 2, in either of the ways, all the parameters: BMI, visceral fat area, diastolic blood pressure and systolic blood pressure have been reduced. For the parameter of visceral fat area, however, the reduction in value measured for the case where both LCD and the exercise are made is about 1.5 times higher than the case where only LCD is made. The same is true for the parameter of systolic blood pressure. Namely, the reduction in value for the case where both LCD and the exercise are made is about 4 times higher than the case where only LCD is made. Thus, it is apparent that there is clear difference in effect present between the ways of body weight reduction.

Making an exercise in the course of body weight reduction is considered to prevent lowering of the energy metabolism at rest condition due to the diet so that the energy consumption is totally increased. Therefore, it is desirable for body weight reduction to combine the diet with the exercise. As the result, the insulin sensitivity, the lipid metabolism of neutral fat and cholesterol, and blood flow to the coronary artery are improved.

In other words, it is possible to analyze reduction in visceral fat and tendency of reduction in blood pressure by the measurement for longer period of time, and to determine whether the body weight reduction is preferable or not depending on the analyzed condition.

Accordingly, an apparatus for measuring visceral fat of the present invention makes possible to calculate the visceral fat area of a person to be measured with higher precision, by using the parameters regarding the blood, for example, blood pressure and pulse rate of the person.

The apparatus of the present invention can further calculate the prevalence rate based on the calculated visceral fat area and body information of the person to determine any possibility of occurrence of some disease caused by the visceral fat area.

In a configuration where the calculated visceral fat area is stored, the apparatus of the present invention determines whether the proper body weight reduction (or diet) is made or not when reduction in visceral fat is seen.

Now, one embodiment of the present invention will be described with reference to the drawings.

Figure 3:
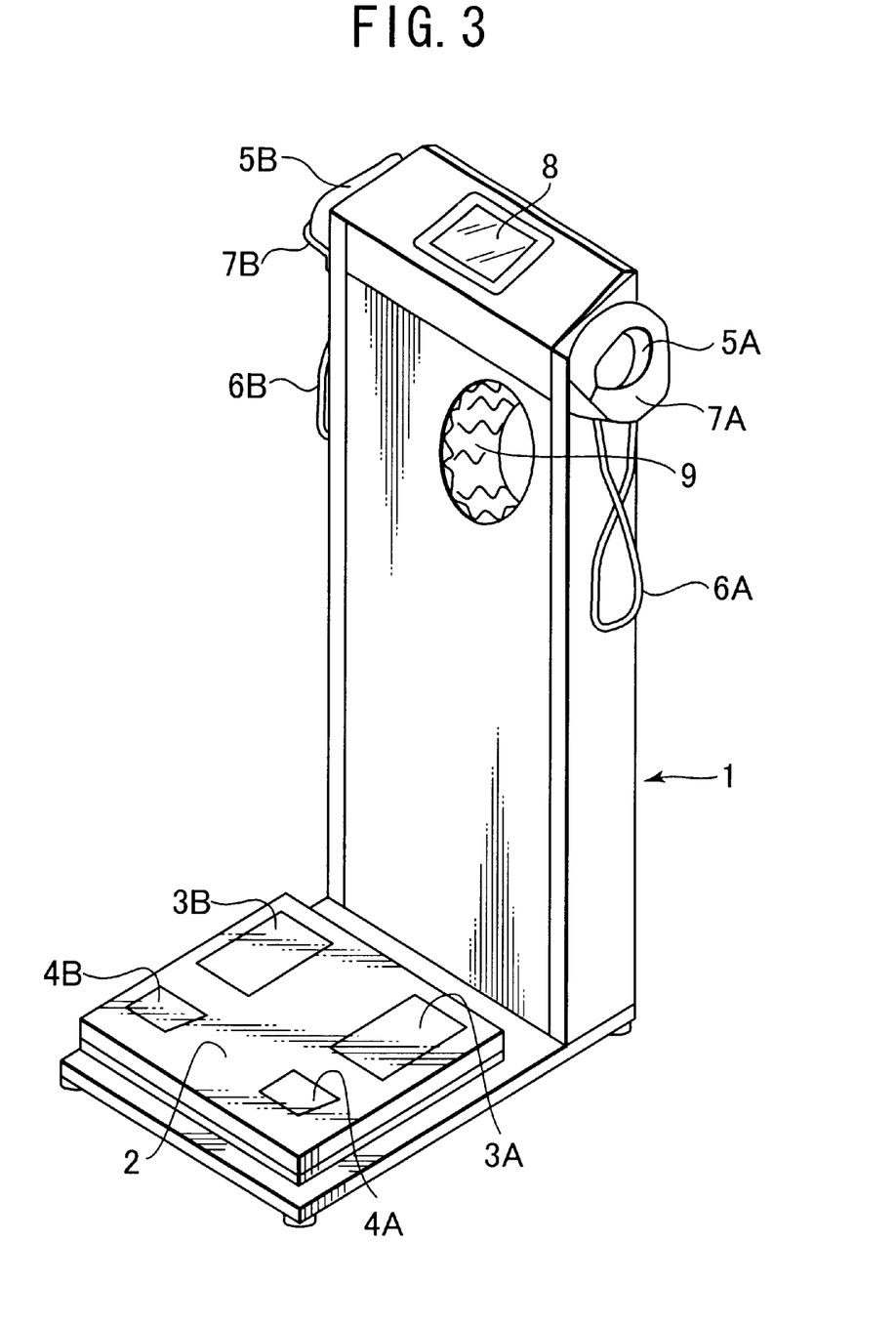
FIG. 3 is an external view of a visceral fat measuring apparatus capable of measuring the visceral fat area of a person to be measured according to one embodiment of the present invention.

FIG. 3 is an external view of a visceral fat measuring apparatus capable of measuring the visceral fat area of a person to be measured according to one embodiment of the present invention. The visceral fat measuring apparatus 1 is configured in the form of a letter "L" and has a conventional body weight meter 2 disposed in the lower portion thereof for measuring the body weight of a person to be measured. Foot electrodes 3A, 3B, 4A and 4B are provided on a measurement surface of the body weight meter 2. The foot electrodes are positioned so that the feet of the person are contact therewith at the time of measurement. In particular, the toe of right foot of the person is contact with the electrode 3A, the toe of left foot is contact with the electrode 3B; the heel of right foot is contact with the electrode 4A; and the heel of left foot is contact with the electrode 4B. The electrodes 3A and 3B are used for supplying an electric current into a living body, and the electrodes 4A and 4B are used for measuring an electric voltage so that the bioelectrical impedance for the living body is determined.

The visceral fat measuring apparatus 1 further includes a right-hand grip 5A and a left-hand grip 5B each connected via each of cords 6A and 6B to the apparatus, and grip holders 7A and 7B secured in both upper side portions for holding the hand grips 5A and 5B, respectively. The hand grips 5A and 5B are held in the grip holders 7A and 7B, except for the time when they are used for measuring the bioelectrical impedance.

The visceral fat measuring apparatus 1 further includes a display unit 8 mounted on the top portion thereof. The display unit 8 may be an LCD module with a touch panel (hereafter simply referred to as a "touch panel") that provides not only a function of displaying the measurement result, some personal information and some wait instruction, but also a function of entering some information through the touch panel. Accordingly, in addition to the personal information such as the height, sex, age, etc. of a person to be measured, several types of other information can be entered by touching to any of switches displayed on the touch panel at the start of measurement.

The visceral fat measuring apparatus 1 further includes a cuff 9 provided through the apparatus from a front surface to a rear surface and configured as a bladder formed from a resilient membrane for measuring blood pressure and pulse rate. The cuff 9 is constructed to pass through an arm of the person and to pressurize it for measuring blood pressure and pulse rate.

Figure 4:
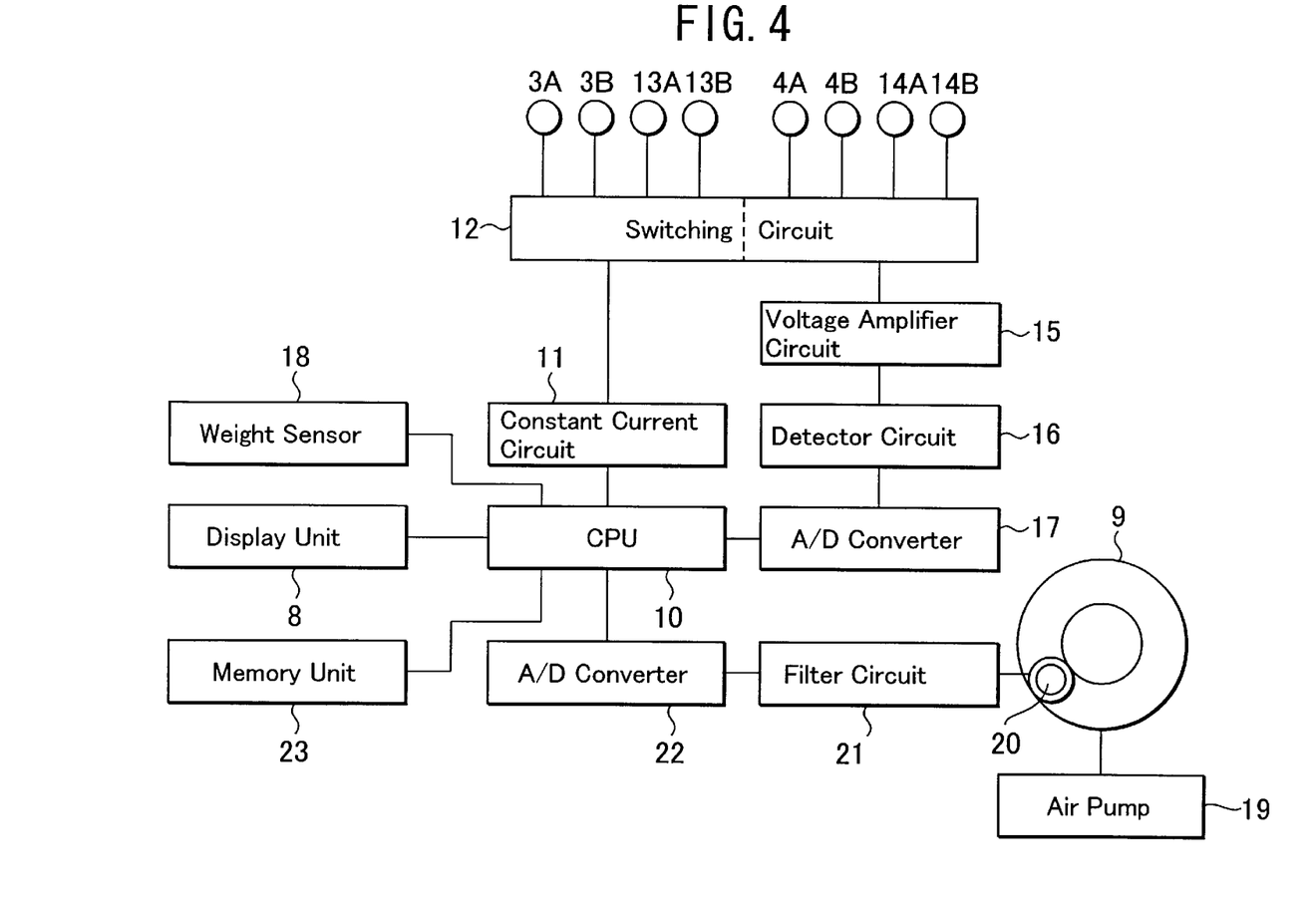
FIG. 4 is a schematic diagram showing an internal circuit of the visceral fat measuring apparatus.

FIG. 4 is a schematic diagram showing an internal circuit of the visceral fat measuring apparatus 1 operated according to the bioelectrical impedance measurement process of the present invention. The visceral fat measuring apparatus 1 includes a CPU 10 acting as an arithmetic and decision means for performing an arithmetic operation and control operation. A constant current circuit 11 is provided for generating a constant current or measurement current according to a process instruction from the CPU 10. The constant current circuit 11 is connected at its output terminal to a switching circuit 12 and hence to the current supplying foot electrodes 3A and 3B and to the current supplying hand electrodes 13A and 13B each on the hand grips 5A and 5B, respectively.

On the other hand, the voltage measurement electrodes 4A and 4B, and the voltage measurement hand electrodes 14A and 14B each on the hand grips 5A and 5B, respectively, are connected through the switching circuit 12 to a voltage amplifier circuit 15 for producing an amplified waveform of the measured voltage value. Thereafter, a detection circuit 16 for shaping the amplified voltage waveform, and an A/D converter 17 for converting the shaped and amplified voltage waveform from analogue to digital format are connected in circuit. The digital signal from the A/D converter 17 is supplied to the CPU 10. The CPU 10 further has a weight sensor 18 of the body weight meter 2 connected thereto for performing the measurement of body weight of the person to be measured.

The cuff 9 whose pressure is adjusted in response to an air flow from an air pump 19 has a pressure sensor 20 incorporated therein. As the pressure in the cuff 9 is increased a cuff pressure signal of the pressure sensor 20 is supplied to a filter circuit 21 for outputting a pulsation signal, which is then converted into a digital signal by an A/D converter 22. This digital signal is supplied to the CPU 10 for calculating the blood pressure value and the pulse rate.

The display unit 8, that is the touch panel having the switching function as the input means, is also connected to the CPU 10 for displaying the information regarding the visceral fat estimated based on the calculated bioelectrical impedance value, body weight value, blood pressure value and pulse rate, as well as the stored personal data of the person to be measured. Accordingly the CPU 10 calculates the bioelectrical impedance value based on the supplied measurement current and the detected measurement voltage, and estimates the body fat ratio or body fat mass based on the calculated bioelectrical impedance value, the body weight and the stored personal information. Those estimated values are then displayed on the display unit 8.

As described above, each of the electrodes is connected through the switching circuit 12. Therefore, the CPU 10 can control to suitably select any ones of the current supplying paths and voltage measuring paths.

Also connected to the CPU 10 is a memory unit 23 for storing the entered personal data, and the measured body weight, visceral fat area, blood pressure, pulse rate, etc.

Now, the visceral fat measuring apparatus 1 according to one embodiment of the present invention is operated as follows. The terms "key" and "switch" used herein means that an input operation is made by touching some portions displayed on touch panel screen of the display 8.

Figure 5:
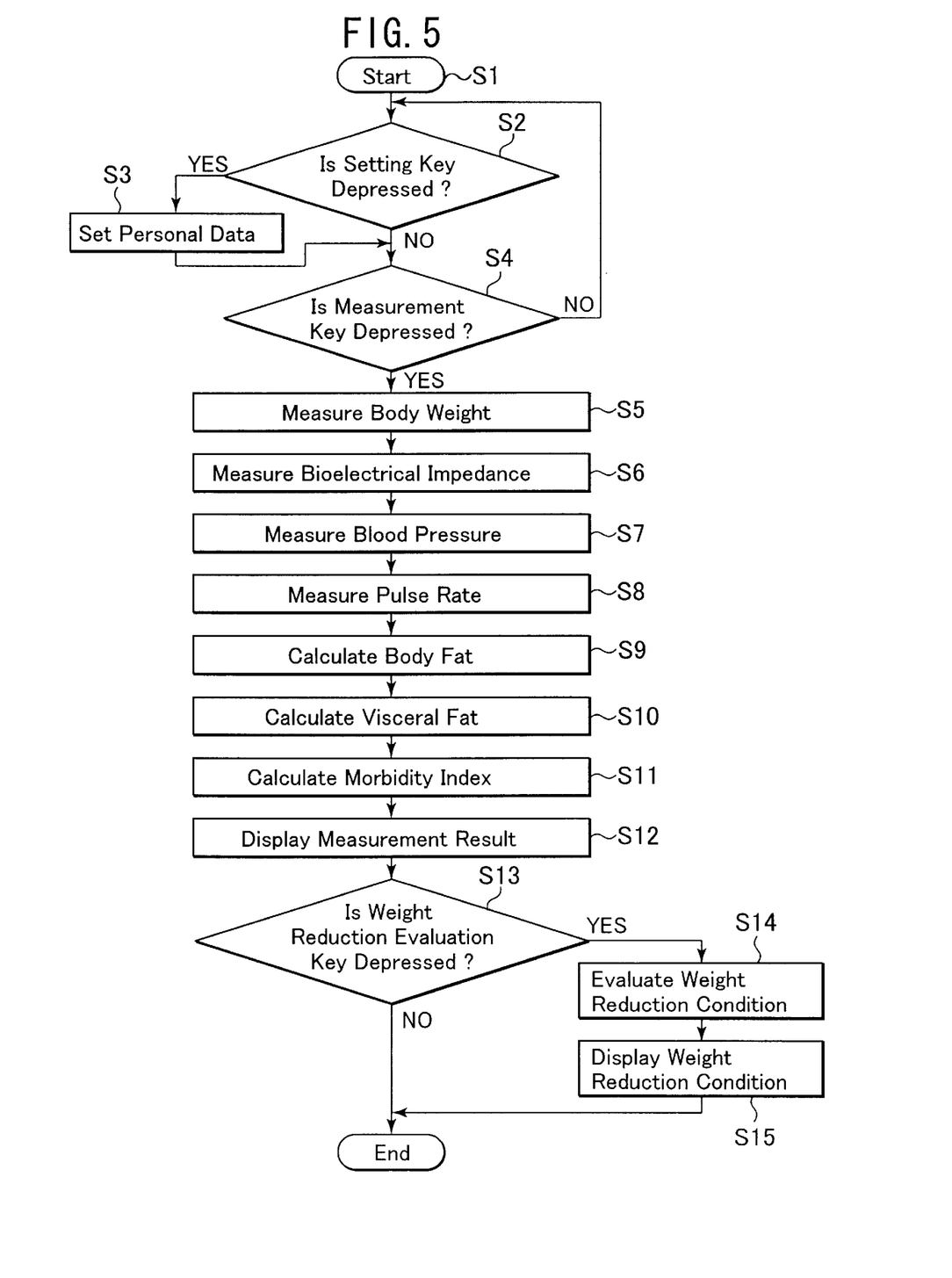
FIG. 5 is a flow chart showing an operation of the visceral fat measuring apparatus.

FIG. 5 is a flow chart showing an operation of the visceral fat measuring apparatus 1 according to the present invention. A person to be measured turns a power switch ON to operate the visceral fat measuring apparatus 1 (Step S1).

When the person depresses the setting key the visceral fat measuring apparatus 1 enters the setting mode (Step S2).

In the setting mode the personal data regarding the body of the person to be measured is set. The up key and the down key are used to modify the values of height, sex, age and girth of the person displayed on the screen. The girth means the girth of the waist or the waist size of the person. Here, the girth of the waist means the girth of the trunk of the person measured at the position of his navel. When depressing the setting key once again the modified value is entered (Step S3).

When the person depresses the measurement key (Step S4) the visceral fat measuring apparatus 1 enters the measurement mode to proceed to Step S5. Otherwise the procedure returns to Step S2 for determining whether the setting key is depressed.

In the measurement mode the person to be measured mounts on the body weight meter 2 and stands at attention.

Then the weight sensor 18 determines that the person has mounted on the weight meter because of change in weight value. The weight value measured after the stabilization of the weight sensor is assumed to be the body weight of the person to be measured (Step S5).

Next, the measurement of bioelectrical impedance of the person to be measured is performed.

The display unit 8 provides a display for prompting the person to be measured to grasp the hand grips 5A and 5B and to contact his body portions with the electrodes. Accordingly the person to be measured contacts the toes of right and left feet with the current supplying electrodes 3A and 3B and the heels of right and left feet with the voltage measurement electrodes 4A and 4B. In addition the person grasps the hand grips 5A and 5B to contact his hands with the electrodes 13A, 13B, 14A and 14B.

Then, a weak high frequency constant current produced by the constant current circuit 11 is fed through any two electrodes selected among the current supplying electrodes 3A, 3B; 13A, 13B into the body of the person to be measured. Thereafter, the bioelectrical impedance of the person is measured between any two electrodes selected among the voltage measurement electrodes 4A, 4B; 14A, 14B using the voltage measurement circuit 24.

The electrodes selected are sequentially switched by the switching circuit 12 to measure the bioelectrical impedance on each of various body portions of the person (Step S6).

Next, the measurement of blood pressure and pulse rate of the person to be measured is performed. The display unit 8 provides a display for prompting the person to pass his arm through the cuff 9. The person then passes his arm through the cuff 9 and depresses the blood pressure measurement key.

The resilient membrane of the cuff 9 inflates with the pressure of air supplied from the air pump 19 controlled by the CPU 10 and squeezes the arm of the person. In such condition the pressure sensor 20 detects an oscillation in pressure due to pulsation of the heart of the person. The detected pressure signal is transmitted to the filter circuit 21 for extracting the pulse wave signal. Then, the pulse wave signal is converted into the digital signal by the A/D converter 22. The digital signal is transmitted to the CPU 10 which calculates the highest and lowest blood pressure and the pulse rate (Steps S7 and S8).

Thereafter, depending on the measured bioelectrical impedance and the stored personal data of the person, the CPU 10 calculates the body fat ratio (Step S9). The detailed description of the calculation of the body fat ratio is omitted, here, because it is well known in the art.

Then, the calculation of the visceral fat area is performed.

The visceral fat area "VFA" is calculated in the following formula using the parameters such as waist size "W" (cm), height "Ht" (cm), body weight "Wt" (kg), age, pulse rate "P", and the difference $\Delta BP$ between the highest and lowest blood pressure of the person to be measured.

$$VFA = a_1 W + b_1 Ht/FFM + c_1(Fat/Ht^2) + d_1 BMI + e_1 Age + f_1 P + g_1 \Delta BP$$

Where $a_1$, $b_1$, $c_1$, $d_1$, $e_1$, $f_1$, and $g_1$ are coefficients; FFM is fat free mass; and Fat is body fat mass. "FFM" and "Fat" can be calculated using the bioelectrical impedance method. The detailed description of such calculation is omitted, here, because it is well known in the art. The body mass index "BMI" is calculated by a formula: "body weight/height$^2$".

Thus the visceral fat area "VFA" is calculated (Step S10).

Next, an arithmetic operation of morbidity index "MI" is performed. In the prior art the "BMI" or body fat ratio is independently used as the parameter to calculate the prevalence ratio. In contrast thereto, according to the present invention, a plurality of such parameters are used for calculation of the prevalence ratio.

The morbidity index "MI" is calculated in the following formula using the parameters such as body mass index "BMI", body fat ratio "%Fat", difference "$\Delta BP$" between the highest and lowest blood pressure values, age "Age", and visceral fat area "VFA".

$$MI = a_2 BMI + b_2 \%Fat + c_2 \Delta BP + d_2 Age + e_2 VFA + f_2$$

Where $a_2$, $b_2$, $c_2$, $d_2$, $e_2$, and $f_2$ are coefficients.

The morbidity index "MI" is represented in the form of quadratic "J" curve. Accordingly it is calculated in the following formula by using a plurality of parameters as one variable.

$$MI = a_3(BMI + \%FAT + \Delta BP + Age + VFA)^2 + b_3(BMI + \%FAT + \Delta BP + Age + VFA) + c_3$$

Where $a_3$, $b_3$ and $c_3$ are coefficients.

Thus the morbidity index "MI" is calculated (Step S11).

Figure 6:
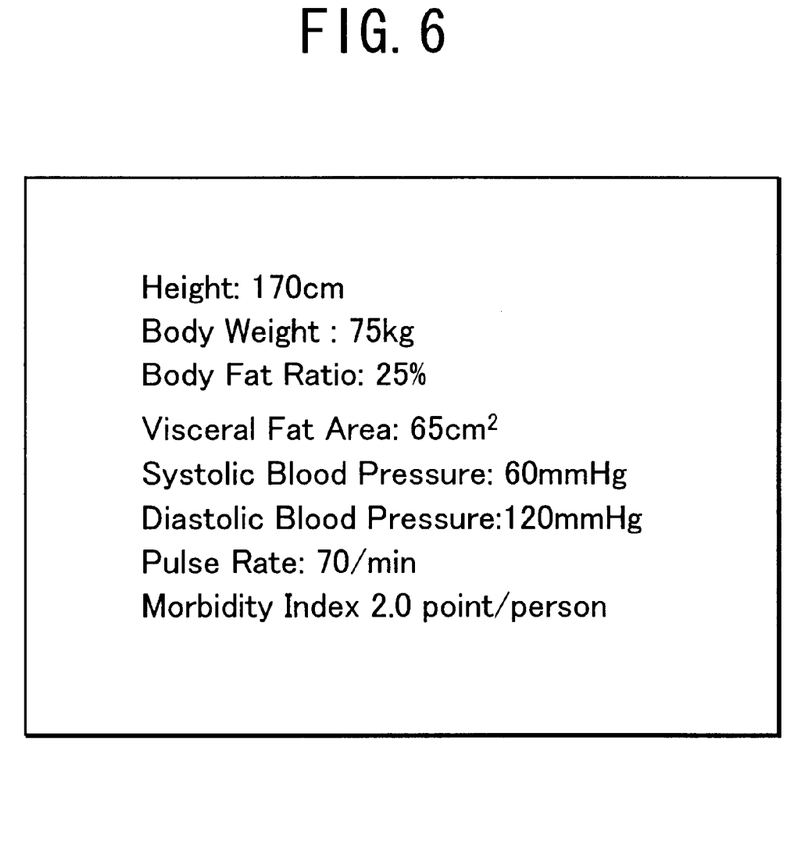
FIG. 6 is a display of measurement result on the screen of the visceral fat measuring apparatus.
Figure 7:
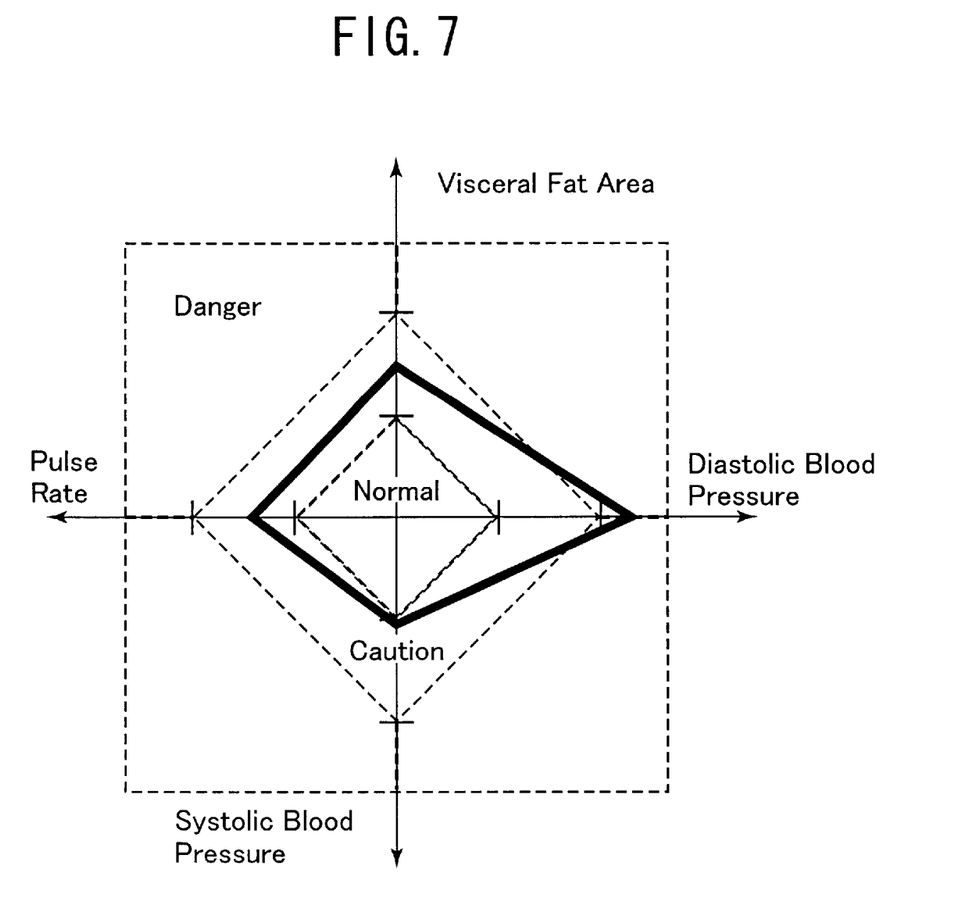
FIG. 7 is a radar chart of the visceral fat measuring apparatus.

Now, the measurement results are displayed. As shown in FIG. 6, the height, body weight, body fat ratio, visceral fat area, systolic blood pressure, diastolic blood pressure, pulse rate and morbidity index of the person to be measured are displayed. At the same time, the visceral fat area, systolic blood pressure, diastolic blood pressure and pulse rate are represented in a radar chart (Step S12), as shown in FIG. 7. In the exemplary case of FIG. 7 the visceral fat area, pulse rate and systolic blood pressure are at the level that needs to pay attention, and in particular, the diastolic blood pressure is at quite higher, dangerous level.

Then, a check is made to determine whether a body weight reduction evaluation key is depressed or not (Step S13). If so, an evaluation for body weight reduction is performed, but if not, the measurement procedure is completed.

The evaluation for body weight reduction is performed as follows:

At first a loss in weight point "LWP" is calculated. The loss in weight point, as used herein, is defined as a value for objectively evaluating the body condition, that is calculated in the following formula by using such amount that changes in weight reduction as the parameter. In this case the body weight "Wt", fat free mass "FFM", difference "BP" between the highest and lowest blood pressure, visceral fat area "VFA", body mass index "BMI" and age "Age" are used as the parameters. However, for the parameters other than the age, the differences between the current values and the previous values stored in the memory 23, or $\Delta Wt$, $\Delta FFM$, $\Delta BP$, $\Delta VFA$ and $\Delta BMI$ are used. The previous value is defined as the value of one month before the current data in order to evaluate the weight reduction for longer period of time. If there is no data of one month before, the oldest data measured in the past may be used.

$$LWP = a_4 \Delta Wt + b_4 \Delta FFM + c_4 \Delta BP + d_4 \Delta VFA + e_4 \Delta BMI + f_4 Age + g_4$$

Where $a_4$, $b_4$, $c_4$, $d_4$, $e_4$, $f_4$, and $g_4$ are coefficients.

Then, the evaluation for body condition is performed using the calculated "LWP" value.

Based on the calculated "LWP" value the body condition is determined as to whether the weight reduction has been attained or not. If so, it is further determined whether the weight reduction has been due to the diet or due to the diet and the exercise. Such evaluation for body condition is performed depending on the range of the "LWP" (Step S14).

Figure 8:
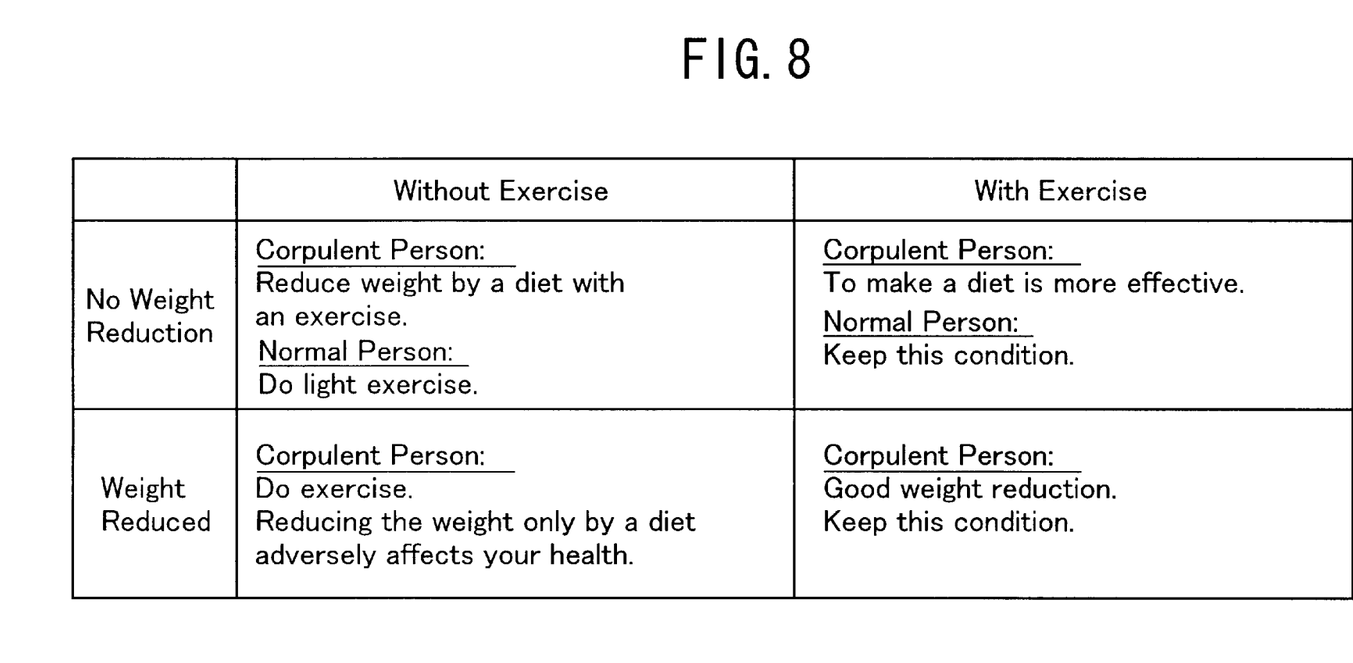
FIG. 8 shows advice messages produced by the visceral fat measuring apparatus.

2≧LWP>1 weight reduction with exercise
1≧LWP>0 weight reduction without exercise
0≧LWP>−1 no weight reduction with exercise
−1≧LWP>−2 no weight reduction without exercise According to such evaluation result some suitable advice message is selected and displayed, as shown in FIG. 8.

Figure 9:
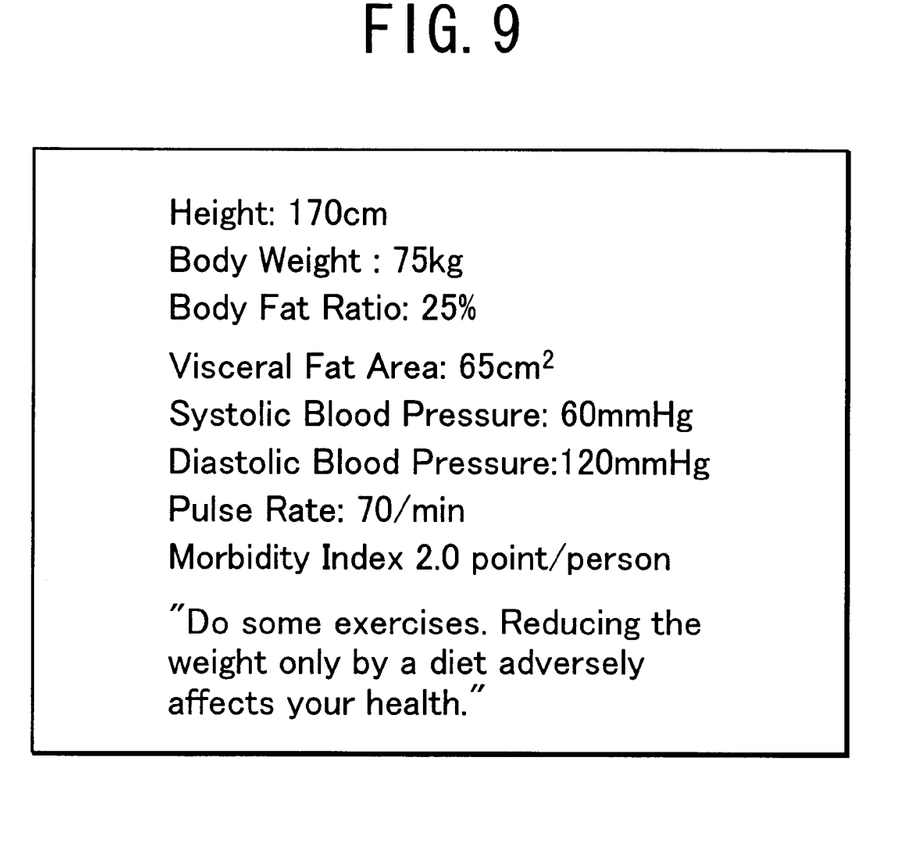
FIG. 9 is a display of measurement result with an advice message on the screen of the visceral fat measuring apparatus.

Then, the total measurement result including the advice message is once again displayed on the display unit 8 (Step S15).

Now, the measurement procedure is terminated.

Figure 10:
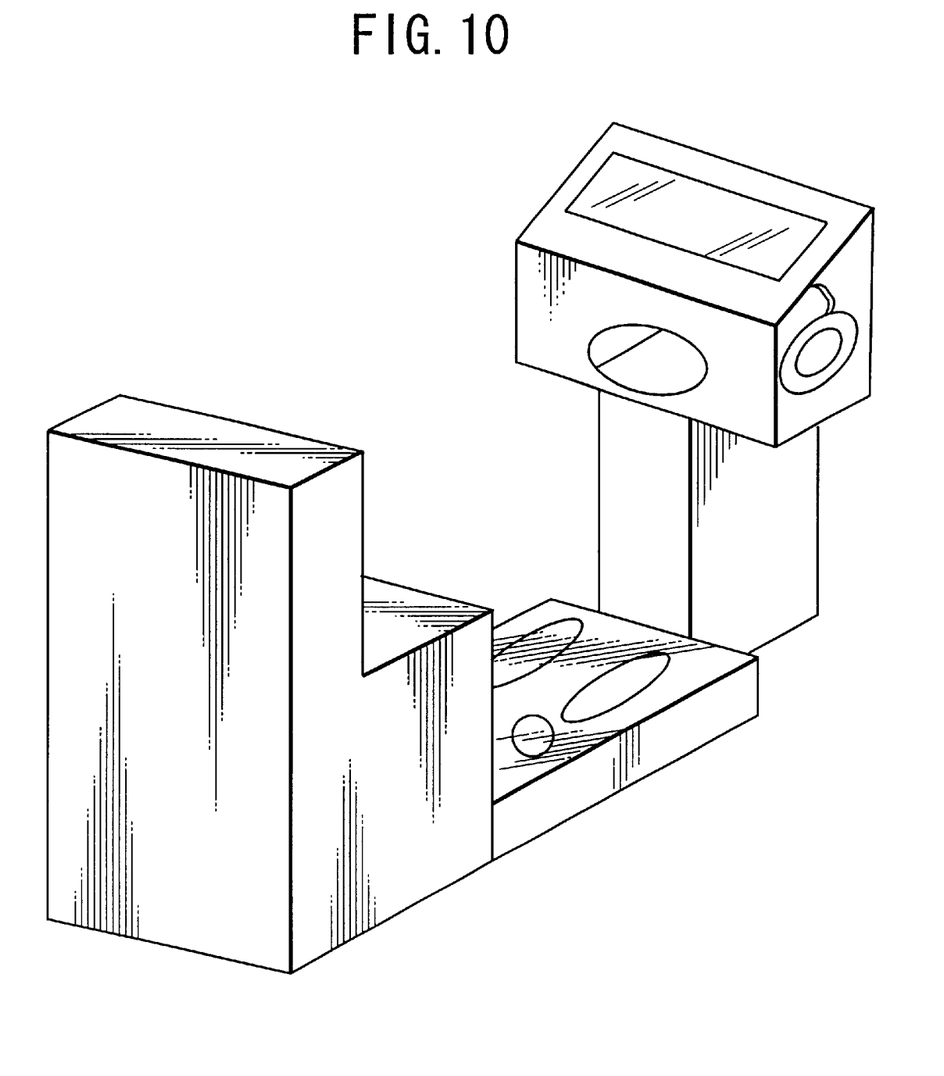
FIG. 10 is an external view of a visceral fat measuring apparatus according to another embodiment of the present invention.

FIG. 10 is an external view illustrating a visceral fat measuring apparatus according to another embodiment of the present invention. The visceral fat measuring apparatus includes a chair on which the person to be measured can sit down. In this case the measurement of bioelectrical impedance and body weight is performed while the person is standing. On the other hand, the measurement of blood pressure and pulse rate is performed while he is sitting down. In general it is preferable that the measurement of blood pressure and pulse rate is performed while the person is in rest condition. Therefore, the visceral fat measuring apparatus that makes possible to measure the blood pressure and pulse rate while the person is sitting down can provide the calculation of visceral fat area with higher precision.

If the chair is provided with a tape measure for measuring the girth of waist of the person there is no need for an additional step of measuring the girth of waist and entering such data.

Although one embodiment of the present invention has been described, the arithmetic equations for calculating visceral fat area, morbidity index and loss in weight point are only for the purpose of illustration, and the present invention is not limited to such equations.

In the embodiment as described above, the apparatus is configured to have the hand and foot electrodes for measuring the bioelectrical impedance in which they are sequentially switched to measure the impedance of a whole body of the person. The present invention, however, is not limited to such configuration, but may be applied to other configuration where the bioelectrical impedance is measured between both hands, between both feet, or between any one hand and any one foot. In other words, the measurement points for the bioelectrical impedance does not have to be limited to any specified points.

In addition, in the embodiment as above, the cuff is used to pressurize the arm of the person for measuring the blood pressure and the pulse rate. The present invention, however, is not limited to such configuration, but the measurement of pulse rate using LEDs or other optical means or an electrocardiogram may be performed.

It is apparent from the foregoing that a visceral fat measuring apparatus according to the present invention includes a cuff that is capable of measuring a blood condition for a person to be measured so that the blood pressure and the pulse rate of the person are measured in addition to the bioelectrical impedance. By taking into account of those values intimately related to the visceral fat, the estimation for the visceral fat can be done with higher precision.

The visceral fat measuring apparatus according to the present invention calculates the morbidity index based on the parameters such as the measured visceral fat area, blood pressure and pulse rate. Therefore, it is significantly effective in that the person can confirm presence or absence of any disease, in addition to the increase/decrease of the visceral fat.

The visceral fat measuring apparatus according to the present invention determines whether undesirable weight reduction only with a diet has been conducted or not, based on change in visceral fat area, blood pressure or pulse rate of the person, and provides the proper advice message to the person accordingly. Therefore, it is significantly effective in that the apparatus can prompt the person to conduct the weight reduction in proper manner of making a diet with an exercise.

What is claimed is:

1. An apparatus for measuring visceral fat, comprising:
   an input unit;
   a bioelectrical impedance measuring unit;
   a blood pressure measuring unit; and
   an arithmetic unit, whereby
   said input unit for entering personal data regarding a body of a person to be measured, said bioelectrical impedance measuring unit measures the bioelectrical impedance of the person, said blood pressure measuring unit measures the blood pressure of the person, and said arithmetic unit calculates the value of visceral fat of the person, based on the entered personal data, the measured bioelectrical impedance and the measured blood pressure.

2. An apparatus for measuring visceral fat, comprising:
   an input unit;
   a bioelectrical impedance measuring unit;
   a pulse rate measuring unit; and
   an arithmetic unit, whereby
   said input unit entering data regarding a body of a person to be measured, said bioelectrical impedance measuring unit measures the bioelectrical impedance of the person, said pulse rate measuring unit measures the pulse rate of the person, and said arithmetic unit calculates the value of visceral fat of the person, based on the entered personal data, the measured bioelectrical impedance and the measured pulse rate.

3. An apparatus for measuring visceral fat, comprising:
   an input unit;
   a bioelectrical impedance measuring unit;
   a blood pressure measuring unit;
   a pulse rate measuring unit; and
   an arithmetic unit, whereby
   said input unit entering data regarding a body of a person to be measured, said bioelectrical impedance measuring unit measures the bioelectrical impedance of the person, said blood pressure measuring unit measures the blood pressure of the person, said pulse rate measuring unit measures the pulse rate of the person, and said arithmetic unit calculates the value of visceral fat of the person, based on the entered personal data, the measured bioelectrical impedance, the measured blood pressure and the measured pulse rate.

4. An apparatus for measuring visceral fat according to any one of claims 1 to 3 in which said arithmetic unit calculates a morbidity index of the person to be measured, based on either the measured blood pressure/and or pulse rate, and the calculated value of visceral fat.

5. An apparatus for measuring visceral fat according to any one of claims 1 to 3 further comprising a memory unit and an evaluation unit, whereby
   said memory unit stores either the measured blood pressure and/or pulse rate, and the calculated value of visceral fat, and
   said evaluation unit evaluates reduced weight condition, based on the previous value of visceral fat and at least one of the blood pressure and pulse rate stored in the memory unit, as well as the calculated current value of visceral fat and at least one of the blood pressure and pulse rate.

6. An apparatus for measuring visceral fat according to claim 5 further comprising a display unit and in which the display unit displays an advice message according to the evaluation result for reduced weight condition.

7. An apparatus for measuring visceral fat according to any one of claims 1 to 3 further comprising a body weight meter, in which the body weight meter measures the body weight of the person and in which the arithmetic unit uses the measured body weight for calculating the value of visceral fat.

8. An apparatus for measuring visceral fat according to any one of claims 1 to 3 in which said value of visceral fat is of visceral fat area.

9. An apparatus for measuring visceral fat according to claim 3 further comprising a display unit and in which the display unit displays at least one of the measured blood pressure and pulse rate as well as the calculated value of visceral fat in the form of radar chart.

* * * * *